United States Patent
D'Aquanni et al.

(10) Patent No.: US 6,740,050 B2
(45) Date of Patent: May 25, 2004

(54) INTRACORPOREAL MEMBER WITH IMPROVED TRANSITION SECTION

(75) Inventors: Peter J. D'Aquanni, Temecula, CA (US); Mo Jafari, Murrieta, CA (US); Mark Richardson, Escondido, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 144 days.

(21) Appl. No.: 09/996,172

(22) Filed: Nov. 27, 2001

(65) Prior Publication Data

US 2003/0100847 A1 May 29, 2003

(51) Int. Cl.[7] .................................................. A61B 5/00
(52) U.S. Cl. ...................................................... 600/585
(58) Field of Search .............................. 600/433–435, 600/585

(56) References Cited

U.S. PATENT DOCUMENTS

| | | |
|---|---|---|
| 4,538,622 A | 9/1985 | Samson et al. |
| 4,748,986 A | 6/1988 | Morrison et al. |
| 5,061,273 A | 10/1991 | Yock |
| 5,135,503 A | 8/1992 | Abrams |
| 5,341,818 A | 8/1994 | Abrams et al. |
| 5,345,945 A | 9/1994 | Hodgson et al. |
| 5,365,942 A * | 11/1994 | Shank .......................... 600/585 |
| 5,636,641 A | 6/1997 | Fariabi |
| 5,788,654 A * | 8/1998 | Schwager .................... 600/585 |
| 6,056,702 A | 5/2000 | Lorenzo |
| 6,491,648 B1 * | 12/2002 | Cornish et al. ............. 600/585 |
| 6,544,197 B2 * | 4/2003 | DeMello ...................... 600/585 |
| 2003/0069521 A1 * | 4/2003 | Reynolds et al. ........... 600/585 |

FOREIGN PATENT DOCUMENTS

| | | |
|---|---|---|
| EP | 0 495 299 A1 | 7/1992 |
| WO | WO 00/32265 | 6/2000 |

* cited by examiner

*Primary Examiner*—Charles Marmor
(74) *Attorney, Agent, or Firm*—Fulwider Patton Lee & Utecht, LLP

(57) ABSTRACT

A guide wire having an elongate core member with a flexible body member disposed about and secured to a core paddle in the distal core section of the elongated core member. A shaping element having a proximal portion is juxtaposed to and secured to the core paddle. The portion of the shaping element distally adjacent to the juxtaposed proximal portion and core paddle has a bending stiffness comparable to the combined bending stiffness of the juxtaposed proximal portion and core paddle. The distal portion of the shaping element may taper so as to have a reduced cross-sectional area in the distal direction, where the portion of the shaping element distally adjacent to the juxtaposed proximal portion and core paddle is enlarged.

12 Claims, 2 Drawing Sheets

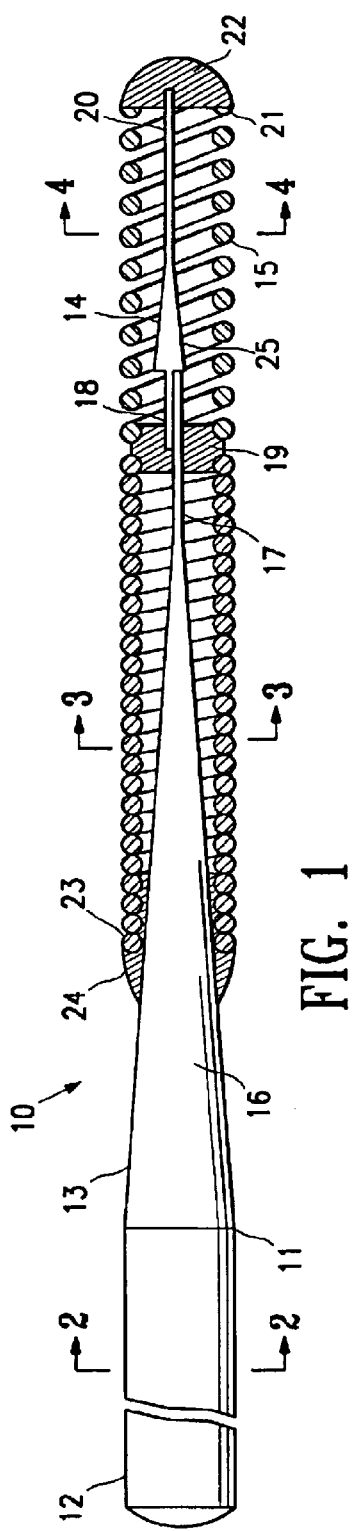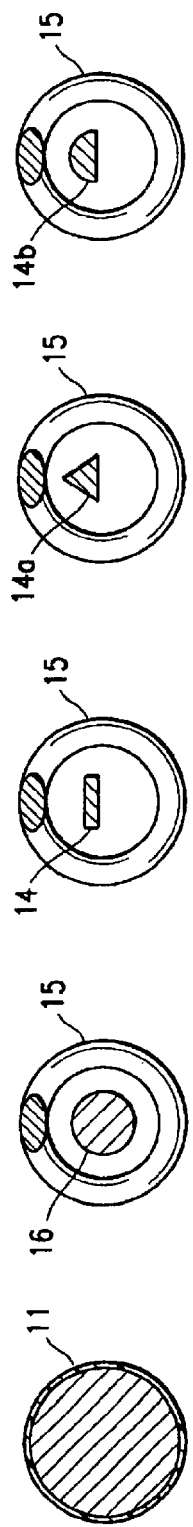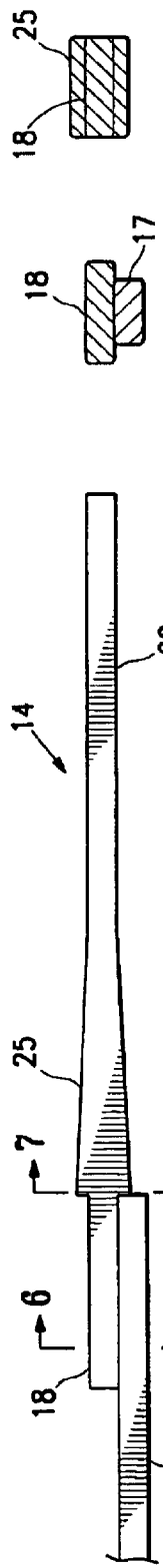

# INTRACORPOREAL MEMBER WITH IMPROVED TRANSITION SECTION

BACKGROUND OF THE INVENTION

This invention relates to the field of advanced medical devices and particularly to intracorporeal devices for performing or aiding in the performance of therapeutic or diagnostic procedures. The intracorporeal devices may be guiding members such as guide wires for advancing intraluminal devices within body lumens. The intracorporeal medical devices include stent delivery catheters, balloon dilatation catheters, atherectomy catheters, electrophysiology catheters and the like.

In a typical percutaneous coronary procedure, a guiding catheter having a pre-formed distal tip is percutaneously introduced into a patient's peripheral artery, e.g., femoral or brachial artery, by means of a conventional Seldinger technique and advanced therein until the distal tip of the guiding catheter is seated in the ostium of a desired coronary artery. A guide wire is first advanced by itself through the guiding catheter until the distal tip of the guide wire extends beyond the arterial location where the procedure is to be performed. Then a catheter (which may be a rapid exchange type catheter such as described in U.S. Pat. No. 5,061,273 to Yock, or an over the wire catheter) is mounted onto the proximal portion of the guide wire which extends out of the proximal end of the guiding catheter which is outside of the patient. The catheter is advanced over the guide wire, while the position of the guide wire is fixed, until the operative element on the catheter is disposed within the arterial location where the procedure is to be performed. After the procedure is performed, the catheter may be withdrawn from the patient over the guide wire or the guide wire repositioned within the coronary anatomy for an additional procedure.

A guide wire may also be used in conjunction with the delivery of an intracoronary stent. One method and system involves disposing a compressed or otherwise small diameter stent about the distal end of a catheter, advancing the catheter through the patient's vascular system over a guide wire until the stent is in the desired location within a blood vessel. The stent is then expanded within the blood vessel, holding the passageway thereof open. The stent may be self-expanding or expanded using an expandable device on the catheter such as a balloon, which after expanding is contracted and withdrawn from the blood vessel. This latter method and system can be used concurrently with balloon angioplasty or subsequent thereto.

Further details of guide wires, and devices associated therewith for various interventional procedures can be found in U.S. Pat. No. 4,748,986 (Morrison et al.); U.S. Pat. No. 4,538,622 (Samson et al.); U.S. Pat. No. 5,135,503 (Abrams); U.S. Pat. No. 5,341,818 (Abrams et al.); and U.S. Pat. No. 5,345,945 (Hodgson, et al.) which are hereby incorporated herein in their entirety by reference thereto.

Conventional guide wires for angioplasty, stent delivery, atherectomy and other intravascular procedures usually have an elongate core member with one or more segments near the distal end thereof which taper distally to smaller cross sections. A flexible body member, such as a helical coil or a tubular body of polymeric material, is typically disposed about and secured to at least part of the distal portion of the core member. A shaping member, which may be the distal extremity of the core member or a separate shaping ribbon which is secured to the distal extremity of the core member, extends through the flexible body and is secured to the distal end of the flexible body by soldering, brazing or welding, or an adhesive in the case of polymeric flexible bodies which forms a rounded distal tip. The leading tip is highly flexible and will not damage or perforate the vessel and the portion behind the distal tip is increasingly stiff which better supports a balloon catheter or similar device.

The shaping member or ribbon of a typical guide wire is a small diameter wire which has been flattened to a relatively constant transverse profile. However, the flattened proximal portion of the shaping member, which is usually attached to a flattened portion of the core member, provides an abrupt change in stiffness along its length which can lead to prolapse during use. Prolapse occurs when the shaping member becomes bent back on itself in a constrained lumen, and is difficult to straighten out with proximal manipulation. There is a need for a shaping member that avoids such prolapse. The present invention satisfies these and other needs.

SUMMARY OF THE INVENTION

The invention is generally directed to a medical device for performing or aiding in the performance of a therapeutic or diagnostic procedure. Specifically, the invention is directed to a guide wire for the introduction or advancement of a medical device into a patient for the performance of a therapeutic or diagnostic procedure.

The guide wire has an elongate core with a proximal core section and a distal core section, an elongated shaping element and a flexible body disposed about and secured to at least part of the distal core section. Preferably, at least part of the distal core section is provided with a surface, herein termed core paddle, which mates with and is preferably secured to a juxtaposed surface of the proximal portion of the shaping element. The elongated shaping element has a distal portion which is secured to the distal end of the flexible body. The portion of the shaping element distally adjacent to the juxtaposed core paddle and proximal portion of the shaping element has a bending stiffness between about 50% and about 150% of the bending stiffness of the two juxtaposed portions. Preferably, the bending stiffness of the distally adjacent portion of the shaping element is not less than about 80%, nor more than about 120% of the juxtaposed portions. Preferably, the bending stiffness of these two regions are essentially the same.

The proximal portion of the shaping element and the mating surface of the core paddle may be flat to ensure contact when secured together. They may be secured together in a suitable manner, e.g., by welding, brazing, soldering, adhesive bonding, mechanical connections and other known joining processes. The core paddle and the shaping element may be formed by coining, rolling or otherwise plastically deforming to a desired shape and dimensions.

The flexible body member disposed about the distal core section and the shaping element may take the form of one or more helical coils, polymer jacket, or the like. The distal end of the flexible body is secured to the distal end of the shaping element, an intermediate portion of the flexible body is preferably secured to the juxtaposed core paddle and proximal portion of the shaping element.

The geometry and dimensions of the juxtaposed portions of the core paddle and the proximal portion of the shaping element and the geometry and dimensions of the shaping element distally adjacent to the juxtaposed portions may be modeled mathematically. While the preferred transverse shapes of the core paddle, the mating portion of the shaping element and the distally adjacent portion of the shaping element are rectangular, other specific transverse shapes may be selected in keeping with the principles of the invention to achieve specific usage requirements.

By providing matching bending stiffness at the shaping element-distal core section junction, the transition over the junction is smooth, so there is little chance for acute or abrupt buckling at the junction.

These and other advantages of the invention will become more apparent from the following detailed description of the invention when taken in conjunction with the accompanying exemplary drawings.

BRIEF DESCRIPTION OF THE DRAWINGS

FIG. 1 is an elevation view, partially in section, of a guide wire embodying features of the invention.

FIG. 2 is a transverse cross-sectional view of the proximal core section of the guide wire shown in FIG. 1 taken along the lines 2—2.

FIG. 3 is a transverse cross-sectional view of the distal core section of the guide wire shown in FIG. 1 taken along the lines 3—3.

FIGS. 4a–4c are transverse rectangular 14, triangular 14a, and D-shaped 14b cross-sections of different embodiments of the proximal core section of the guide wire shown in FIG. 1 taken along the lines 4—4.

FIG. 5 is an enlarged partial elevational view of the junction between the shaping element and the core paddle shown in FIG. 1.

FIG. 6 is a transverse cross-section view of the juxtaposed proximal portion of the shaping element and the core paddle shown in FIG. 5 taken along the lines 6—6.

FIG. 7 is a transverse cross-sectional view of the enlarged portion of the shaping element shown in FIG. 5 taken along the lines 7—7.

DETAILED DESCRIPTION OF THE PREFERRED EMBODIMENTS

Figure 9:
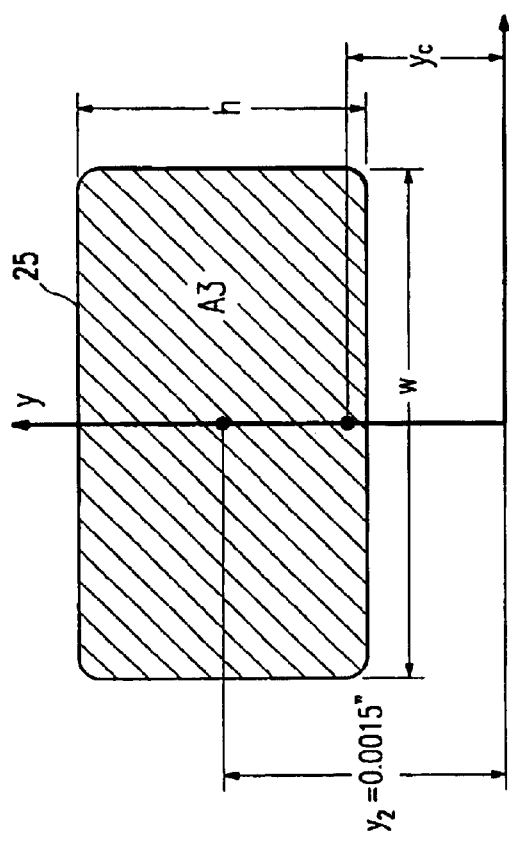
FIG. 9 is an enlarged transverse cross-sectional view shown in FIG. 7 referencing the center of gravity of the enlarged portion of the shaping element.

FIGS. 1–4 illustrate an embodiment of a guide wire 10 which includes an elongated core member 11, with a proximal core section 12, a distal core section 13, a shaping element 14 and a flexible body member or coil 15 which is disposed about and secured at one or more locations to the distal core section 13. The distal core section 13 has a tapered core segment 16 and a flexible core segment or paddle 17 which is distally contiguous to the tapered core segment. The proximal portion 18 of the shaping element 14 is flattened and secured to the juxtaposed flattened core paddle 17 by suitable means. The juxtaposed core paddle 17 and proximal portion 18 of the shaping element 14 are secured to the coil 15 by a mass of solder or weld 19. The distal portion 20 of the shaping element 14 is secured to the distal end 21 of coil 15 by rounded mass or plug 22 of solder or weldment. The proximal end 23 of the coil 15 is similarly bonded or secured to the distal core section 13 by a body of solder 24.

Regions of abrupt stiffness changes in the guide wire are potential areas for prolapse. As shown in greater detail in FIGS. 5–7, the shaping element 14 has an enlarged portion 25 distally adjacent to the proximal portion 18 secured to the core paddle 17 which distally tapers to smaller and relatively constant transverse dimensions. By enlarging the cross-sectional area of the shaping element 14 just distal to the overlapping junction between the distal core section 13 and the shaping element 14, or decreasing the area of the junction between the core section 13 and shaping element 14, the bending stiffness progresses through a smooth transition. The enlarged portion 25 of the shaping element 14 should have approximately the same bending stiffness of juxtaposed junction between the distal core section 13 and proximal portion 18 of the shaping element 14. The bending stiffness of the enlarged portion 25 of the shaping element 14 should be between about 50% and about 150% of the bending stiffness of juxtaposed junction between the distal core section 13 and the shaping element 14. Preferably, the bending stiffness of these two regions are essentially the same.

The shaping element 14 preferably has a gradually decreasing bending stiffness in the distal direction. The distal portion 20 of the shaping element 14 may taper in the distal direction from the enlarged portion 25 in the transverse dimensions of height, width, or both. There may be a gradual reduction with cross-sectional area along a portion of the shaping element 14 in the distal direction from the enlarged portion 25. The distal portion 20 of the shaping element 14 may have a D-shaped or triangular cross-section along the longitudinal axis as shown in FIGS. 4b and 4c. Preferably, the bending stiffness gradually changes, starting at the shaping element 14 and through the junction between the distal core section 13 and the shaping element 14 to the proximal core 12.

The shaping element 14 has a length typically ranging about 1 to about 12 cm, preferably about 2 to about 5 cm, although longer segments may be used. The transverse dimensions may be varied.

The distal section 13 may also have more than one tapered segment 16 which have typical distally decreasing tapers with substantially round transverse cross sections, such as described in U.S. patent application Ser. No. 08/868,764, filed Jun. 4, 1997 (Cornish, et al.) entitled STEERABLE GUIDE WIRE WITH ENHANCED DISTAL SUPPORT, which is hereby incorporated by reference in its entirety. The core member 11 or one or more portions thereof may be formed of stainless steel, NiTi alloys or combinations thereof such as described in U.S. Pat. No. 5,341,818 (Abrams et al.) which has been incorporated herein. Other materials such as the high strength alloys described in U.S. Pat. No. 5,636,641 (Fariabi), entitled HIGH STRENGTH MEMBER FOR INTRACORPOREAL USE, which is incorporated herein by reference, may also be used. The core member 11 may be optionally coated with a lubricious coating such as a fluoropolymer, e.g., TEFLON® available from DuPont, which extends at least the length of the proximal core section 12. The distal section 13 is also provided with a lubricous coating, such as a MICRO-GLIDE™ coating used by the present assignee, Advanced Cardiovascular Systems, Inc. on many of its commercially available guide wires. Hydrophilic coatings may also be employed.

The overall length and diameter of guide wire 10 may be varied to suit the particular procedures in which it is to be used and the materials from which it is constructed. The length of the guide wire 10 generally ranges from about 65 cm to about 320 cm, more typically ranging from about 160 cm to about 200 cm. Commercially available guide wires for coronary anatomy, typically have lengths of about 175 cm or about 190 cm. Guide wire diameters generally range from about 0.008 inch to about 0.035 inch (0.2 mm to 0.9 mm), more typically ranging from about 0.01 inch to about 0.018 inch (0.25 mm to 0.55 mm). Commercially available guide wires for coronary use are typically about 0.01, 0.012 and 0.014 inch (0.25, 0.3 and 0.036 mm respectively) in diameters.

The wire from which the coil 14 is made generally has a transverse diameter of about 0.001 to about 0.004 inch (0.025–0.1 mm), preferably about 0.002 to about 0.003 inch (0.05–0.08 mm). Multiple turns of the distal portion of coil 14 may be expanded to provide additional flexibility. The helical coil 14 may have a diameter or transverse dimension that is about the same as the proximal core section 12. The coil 14 may have a length of about 2 cm to about 40 cm or more, preferably about 2 cm to about 10 cm in length and may at least in part be formed of a suitable radiopaque material such as platinum, palladium or alloys thereof or formed of other material such as stainless steel and coated with a radiopaque material such as gold. The coil 14 may be replaced with a flexible body member formed of a polymeric material such as polyimide, polyethylene, polyurethane, TFE, PTFE, ePTFE and other similar materials.

Figure 8:
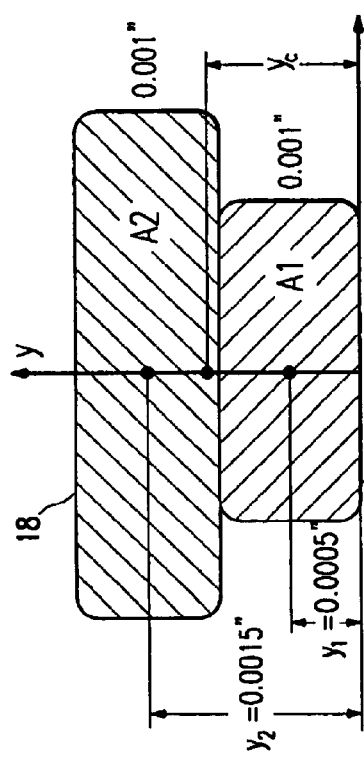
FIG. 8 is an enlarged transverse cross-sectional view shown in FIG. 6 referencing centers of gravity of the portions for determining moment of inertial thereof.

Reference is made to FIGS. 8 (referred to hereinafter as section 1) and 9 (referred to hereinafter as section 2) which are enlarged views of the transverse cross-sections shown in FIGS. 6 and 7. In this embodiment, the proximal portion of the shaping element 14 is formed of stainless steel and the core paddle is formed of a superelastic NiTi alloy. The cross-section of section 1 (FIG. 8) and the cross section of section 2 (FIG. 9) should be designed to have similar bending stiffness by considering both the Young's Modulus of the materials ($E_{nt}$ and $E_{ss}$) and the centroidal moment of inertia of the cross-section (I) in order for the joint to have a smooth transition in bending stiffness over the joint: This relationship is shown by $$(EI)_{sect1} = (EI)_{sect2} \quad (1)$$

Because the joint usually involves at least one cross-section that incorporates two materials (i.e., overlapped flats, such as that in section 1), E and I must be calculated as composite values.

For the calculation of a composite Young's modulus ($E_{tot}$) for the overlapped section, the proportional contribution equation is used:

$$E_{tot} = E_{ss}A_{ss} + E_{nt}A_{nt} \quad (2)$$

Where:

$E_{tot}$=composite Young's modulus $E_{ss}$=Young's modulus of stainless steel material $A_{ss}$=% of cross-sectional area of stainless steel material $E_{nt}$=Young's modulus of NiTi material $A_{nt}$=% of cross-sectional area of NiTi material The composite centroidal moment of inertia ($I_{tot}$) is computed as the sum of the moments of inertia about the centroidal axis of the different parts:

$$I_{tot} = \sum I_{ci} = I_{c1} + I_{c2} \quad (3)$$

The modulus of stainless steel is about 29 Msi (199.3 GPa) and that of NiTi alloy 12 Msi (82.5 GPa). If the proximal portion of the stainless steel shaping element has a rectangular transverse cross-section 0.001 inch×0.006 inch (0.0025 cm×0.015 cm) and if the paddle of the NiTi core, which overlaps the proximal portion of the shaping element, has a rectangular transverse cross-section 0.001 inch×0.004 inch (0.0025 cm×0.010 cm) then the percent cross-sectional areas are calculated $$A_{SS} = \frac{(0.001 \text{ in})(0.006 \text{ in})}{(0.001 \text{ in})(0.006 \text{ in}) + (0.001 \text{ in})(0.004 \text{ in})} = 0.60$$

$$A_{NT} = \frac{(0.001 \text{ in})(0.004 \text{ in})}{(0.001 \text{ in})(0.006 \text{ in}) + (0.001 \text{ in})(0.004 \text{ in})} = 0.40$$

Equation 2 becomes $$E_{tot} = (29 \text{ Msi})(0.60) + (12 \text{ Msi})(0.40) = 22 \text{ Msi or } 151.2 \text{ GPa}$$

In order to calculate the composite centroid moment of inertia ($I_{TOT}$), the centroid ($y_c$) of the overlapped sections must be determined from the equation.

$$y_c = \frac{\sum_i A_i y_i}{\sum_i A_i}$$

$$y_C = \frac{A_{SS}y_{SS} + A_{NT}y_{NT}}{A_{SS} + A_{NT}}$$

$$= \frac{(0.001 \text{ in})(0.006 \text{ in})(0.0015 \text{ in}) + (0.001 \text{ in})(0.004 \text{ in})(0.0005 \text{ in})}{(0.001 \text{ in})(0.006 \text{ in}) + (0.001 \text{ in})(0.004 \text{ in})}$$

$$= .0011 \text{ in or } 0.0028 \text{ cm}$$

The distances (y) are shown in FIG. 8.

With the centroidal axis of $y_c$=0.0011 inch (0.0028 cm), the moment of inertia of each component may be calculated about this axis:

$$I_C = I_X + Ad^2$$

Where:

$I_C$=the moment of inertia of each component about the centroidal axis of the entire section $I_X$=the moment of inertia of each component about its own centroidal axis A=the cross-sectional area of the component d=the distance from the component's centroidal axis to the calculated centroidal axis of the overlapped section For the overlapping proximal portion of the stainless steel shaping element:

$$(I_C)_{SS} = 1/12 \, bh^3 + Ad^2$$

$$= 1/12(0.006 \text{ in})(0.001 \text{ in})^3 +$$

$$(0.001 \text{ in})(0.006 \text{ in})(0.0015 - 0.0011 \text{ in})^2$$

$$= 1.46 \times 10^{-12} \text{ in}^4 \text{ or } 6.08 \times 10^{-11} \text{ cm}^4$$

For the flattened core paddle:

$$(I_C)_{NT} = 1/12 \; bh^3 + Ad^2$$

$$= 1/12(0.004 \text{ in})(0.001 \text{ in})^3 +$$

$$(0.001 \text{ in})(0.004 \text{ in})(0.0011 - 0.0005 \text{ in})^2$$

$$= 1.77 \times 10^{-12} \text{ in}^4 \text{ or } 7.37 \times 10^{-11} \text{ cm}^4$$

The total moment of inertia of section 1 is the sum of the two parts:

$$I_{TOT} = (I_C)_{SS} + (I_C)_{NT}$$

$$= 1.46 \times 10^{-12} + 1.77 \times 10^{-12}$$

$$= 3.23 \times 10^{-12} \text{ in}^4 \text{ or } 1.34 \times 10^{-10} \text{ cm}^4$$

So the bending stiffness of section 1 is:

$$E_{TOT}I_{TOT} = (22 \text{ Msi})(3.23 \times 10^{-12} \text{ in}^4)$$

$$= 7.11 \times 10^{-5} \text{ (lb)(in}^2\text{) or } 2.04 \times 10^{-3} \text{ (N)(cm}^2\text{)}$$

Having calculated the bending stiffness of section 1 comprising the proximal portion 18 of shaping element 14 and the core paddle 17, then the adjacent section 2 of the enlarged portion 25 of the shaping element 14 can be readily designed to have the same or approximately the same bending stiffness. As a further example, following the design shown in FIGS. 5–7 where the base (or width) of the enlarged portion 25 of the shaping element 14 is the same as the base or width of the proximal portion 18 of the shaping element 14, then the height of the enlarged portion 25 is the only unknown.

In order to find the height of the enlarged portion 25, the bending stiffness of the enlarged portion is calculated using the moment of inertia about the centroid of this section. This value is calculated as a standard moment of inertia about a centroidal axis. In this case, it is a rectangular section, so the formula is:

$$I_x = \tfrac{1}{12} bh^3$$

Going back to equation 1, $(EI)_{SECT1}$ has already been calculated, and it is known that E for section 2 is $E_{SS}$, or 29 Msi. Using the equation above, $E_{SS}$, and the calculated bending stiffness of section 1, the height of the enlarged portion 25 ($h_{SECT2}$) can be solved as follows:

$$(EI)_{SECT1} = (EI)_{SECT2}$$

$$(EI)_{SECT1} = E_{SS} I_{SECT2}$$

$$(EI)_{SECT1} = E_{SS}(1/12 \, b_{SECT2} h_{SECT2}^3)$$

$$h_{SECT2} = \sqrt[3]{\frac{12(EI)_{SECT1}}{b_{SECT2} E_{SS}}}$$

Substitute in the known values and solve:

$$h_{SECT2} = \sqrt[3]{\frac{12(7.11 \times 10^{-5} \text{ (lb)(in}^2\text{))}}{(0.006 \text{ in})(29 \text{ Msi})}} = 0.0017 \text{ inch or } 0.0043 \text{ cm}$$

From this, the height required for the enlarged portion 25 to have the same bending stiffness as the juxtaposed proximal portion 18 and core paddle 17, is 0.0017 inch (0.0043 cm).

Figure 10:
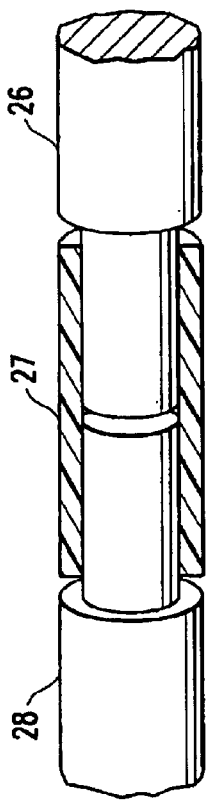
FIG. 10 is a partial elevational view of a guide wire having two core sections joined with a hypotube.

It will be apparent from the foregoing that, while particular forms of the invention have been illustrated and described, various modifications can be made without departing from the spirit and scope of the invention. For example, while the invention is described herein in terms of a junction between a core paddle and the proximal portion of a shaping member, those skilled in the art will recognize that the same features can be utilized in a junction of other components such as hypotube components. This can be seen in FIG. 10, where a hypotube 27 is used to join a proximal core section 28 to a distal core section 26. Typically, the distal core section 26 and the hypotube 27 are composed of NiTi, while the proximal core section 28 is stainless steel. It is also contemplated that the features of the invention described herein could be utilized in a junction where the proximal core section and the distal core section are soldered together without the use of a hypotube.

Those skilled in the art will recognize that features shown in one embodiment of the invention may be utilized in other embodiments of the invention. To the extent not otherwise described herein, the materials and methods of construction and the dimensions of conventional intravascular guide wires may be employed with the guiding member embodying features of the present invention. While the description of the invention is directed to embodiments for coronary applications, various modifications and improvements can be made to the invention without departing therefrom. Additionally, reference to the terms "members," "elements," "sections," and terms of similar import in the claims which follow shall not be interpreted to invoke the provisions of 35 U.S.C. §112 (paragraph 6) unless reference is expressly made to the term "means" followed by an intended function.

What is claimed:

1. A guide wire for intracorporeal procedures, comprising:
a core member having a proximal core section and a distal core section;
a shaping element having a distal portion and a proximal portion, the proximal portion being juxtaposed to at least part of the distal core section, the shaping element further having an enlarged portion distally adjacent to the proximal portion juxtaposed to the distal core section, the enlarged portion having a bending stiffness between about 50% and about 150% of the bending stiffness of the juxtaposed portions of the distal core section and the proximal portion of the shaping member; and
a flexible body disposed about the distal core section and the distal portion of the shaping member,
wherein the distal core section includes a paddle portion having a flat longitudinal surface and the proximal portion of the shaping element has a flat longitudinal surface, the flat surface of the paddle portion and the proximal portion being secured together.

2. The guide wire of claim 1, wherein the shaping element has a gradual reduction of cross-section area along a portion of its length from the enlarged portion in the distal direction.

3. The guide wire of claim 1, wherein the shaping element has a gradually decreasing bending stiffness along a portion of its length from the enlarged portion in the distal direction.

4. The guide wire of claim 1, wherein the distal portion of the shaping element tapers in the distal direction from the enlarged portion in at least one transverse dimension.

5. The guide wire of claim 4, wherein the at least one transverse dimension is the width.

6. The guide wire of claim 4, wherein the at least one transverse dimension is the height.

7. The guide wire of claim 1, wherein the shaping element tapers in the distal direction from the enlarged portion in at least two transverse dimensions such that the cross-sectional area of the shaping element decreases in the distal direction.

8. The guide wire of claim 1, wherein the shaping element has a length between about 1 cm to about 12 cm.

9. The guide wire of claim 1, wherein the distal portion of the shaping element has a D-shaped longitudinal cross section.

10. The guide wire of claim 1, wherein the distal portion of the shaping element has a triangular shaped longitudinal cross section.

11. A guide wire for intracorporeal procedures, comprising:

a core member having a proximal core section and a distal core section;

a shaping element having a distal portion and a proximal portion, the proximal portion being juxtaposed to at least part of the distal core section, the shaping element further having an enlarged portion distally adjacent to the proximal portion juxtaposed to the distal core section, the enlarged portion having a bending stiffness between about 50% and about 150% of the bending stiffness of the juxtaposed portions of the distal core section and the proximal portion of the shaping member; and a flexible body disposed about the distal core section and the distal portion of the shaping member, wherein the distal portion of the shaping element has a D-shaped longitudinal cross section.

12. A guide wire for intracorporeal procedures, comprising:

a core member having a proximal core section and a distal core section;

a shaping element having a distal portion and a proximal portion, the proximal portion being juxtaposed to at least part of the distal core section, the shaping element further having an enlarged portion distally adjacent to the proximal portion juxtaposed to the distal core section, the enlarged portion having a bending stiffness between about 50% and about 150% of the bending stiffness of the juxtaposed portions of the distal core section and the proximal portion of the shaping member; and a flexible body disposed about the distal core section and the distal portion of the shaping member, wherein the distal portion of the shaping element has a triangular shaped longitudinal cross section.

* * * * *